United States Patent [19]

Ziegler

[11] Patent Number: 4,474,141

[45] Date of Patent: Oct. 2, 1984

[54] HEAT EXCHANGER FOR COOLING A HOT GAS

[75] Inventor: Georg Ziegler, Winterthur, Switzerland

[73] Assignee: Sulzer Brothers Ltd., Winterthur, Switzerland

[21] Appl. No.: 460,782

[22] Filed: Jan. 25, 1983

[30] Foreign Application Priority Data

Feb. 3, 1982 [CH] Switzerland .......................... 656/82

[51] Int. Cl.³ .............................................. F22B 1/02
[52] U.S. Cl. ......................................... 122/32; 165/75
[58] Field of Search .............. 122/32, 33, 209 R, 221, 122/222, 224, 227, 230, DIG. 14; 165/81, 75

[56] References Cited

U.S. PATENT DOCUMENTS 3,325,374 6/1967 Margen .............................. 122/32 X
3,930,537 1/1976 Wolowodik ........................ 122/32 X Primary Examiner—Edward G. Favors
Attorney, Agent, or Firm—Francis C. Hand

[57] ABSTRACT

The heat exchanger includes a cylindrical pressure vessel in which a faller column having heat exchange surfaces and at least one riser column having further heat exchange surfaces are mounted. The riser column walls extend around the walls of the faller column. The top part of the pressure vessel is connected to a bottom part in a dis-connectable manner with the riser column walls being suspended in the bottom part. The walls of the faller column with all the heating surfaces disposed therein can be withdrawn from the space around which the riser column walls extend for servicing.

13 Claims, 5 Drawing Figures

HEAT EXCHANGER FOR COOLING A HOT GAS

This invention relates to a heat exchanger for cooling gases. More particularly, this invention relates to a heat exchanger for cooling gases contaminated with solid particles.

As is known, various types of heat exchangers have been used for cooling gases, such as a synthesis gas, which are contaminated with solid particles. For example U.S. patent application Ser. No. 421,313 describes a heat exchanger having a faller column disposed within a cylindrical pressure vessel along with at least one riser column. The riser column walls extend around the faller column walls and each column is provided with heat exchange surfaces so that a flow of hot gas can be cooled during descent through the faller column as well as during ascent through the riser column. In addition, a deflecting chamber has been disposed at the bottom of the columns into which the solid particles can be separated and subsequently removed.

However, it has been found that fairly complicated and elaborate measures have to be taken with this type of heat exchanger in order to obtain access to the heat exchange surfaces on which solid particles tend to be deposited for servicing purposes.

Accordingly, it is an object of the invention to provide a heat exchanger for cooling gases which is of improved construction for servicing purposes.

It is another object of the invention to simplify the construction of a heat exchanger for cooling hot gases.

It is another object of the invention to provide a heat exchanger which can be readily serviced.

Briefly, the invention provides a heat exchanger for cooling a hot gas which is comprised of a pressure vessel having a top part and a bottom part releaseably secured to each other, a faller column having a plurality of walls disposed in the top part and extending into the bottom part and at least one riser column having a plurality of walls secured to and disposed within the bottom part laterally of the faller column. The arrangement of the faller column and riser column is such that upon separation and movement of the top part of the pressure vessel relative to the bottom part, the faller column can be withdrawn from the bottom part in order to permit access to the riser column, for example for cleaning or other servicing purposes.

After being withdrawn, the faller column can be inspected from above and below and, if necessary, given pull-through cleaning. After the faller column has been removed, the riser column can be readily inspected and, if necessary, serviced from the faller column access space.

The faller column is also provided with a plurality of heat exchange surfaces which depend into the bottom part of the pressure vessel for cooling a flow of hot gas passing downwardly thereover. Likewise, the riser column is provided with a plurality of heat exchange surfaces for cooling a flow of gas passing upwardly thereover.

In order to improve accessability of the heat exchange surfaces in the riser column, two or more riser columns can be disposed about the faller column in parallel relation. Where multiple riser columns are used, the cross-section of each riser column is flatter than where just one riser column is provided.

In order to facilitate withdrawal of the faller column, the faller column walls are suspended on the top part of the pressure vessel. This avoids the need for any separation work on the top of the pressure vessel.

The faller column walls may also include sealingly interconnected tubes which form an evaporator heating surface. This provides the advantage that the outside surfaces of the faller column walls may also serve as a wall of one or more riser columns. Further, these walls can be very readily serviced.

The heat exchanger may have a line for supplying the heating surfaces with a working medium such as water. This line may be extended through the faller column from the top part of the vessel or may be eliminated. In the latter cases, at least one distributor is connected to the tubes of the faller column at a lower end, a feed line is extended through the pressure vessel and riser column wall to the distributor to deliver the working medium and a resilient line section is connected between and to the feed line and distributor. However, in order to remove the faller column, the deflecting chamber must be entered and the resilient line section to the distributor must be separated.

The faller column may also include a plurality of tubes which form intermediate walls and which have lower ends connected to the distributor. This provides a simplification of the construction of the faller column.

Further, the tubes forming the intermediate walls and outer walls of the faller column may be separated into two sets with one set connected to one distributor and one collector while the other set of tubes is connected to a second distributor and a second collector. This subdivision into two groups enables the dismantled faller column to be opened up fairly readily for inspection, cleaning and/or repair by simply opening up two straight longitudinal seams and one peripheral seam of the faller column.

The riser column walls are disposed and connected so as to be vertically resilient relative to the pressure vessel in order to take-up heat expansion. In addition, the riser column walls are connected to the pressure vessel to be vertically stationary. Further, soot blowers can be extended from the side to the walls of the pressure vessel and each riser column.

These and other objects and advantages of the invention will become more apparent from the following detailed description taken in conjunction with the accompanying drawings wherein.

Figure 1:
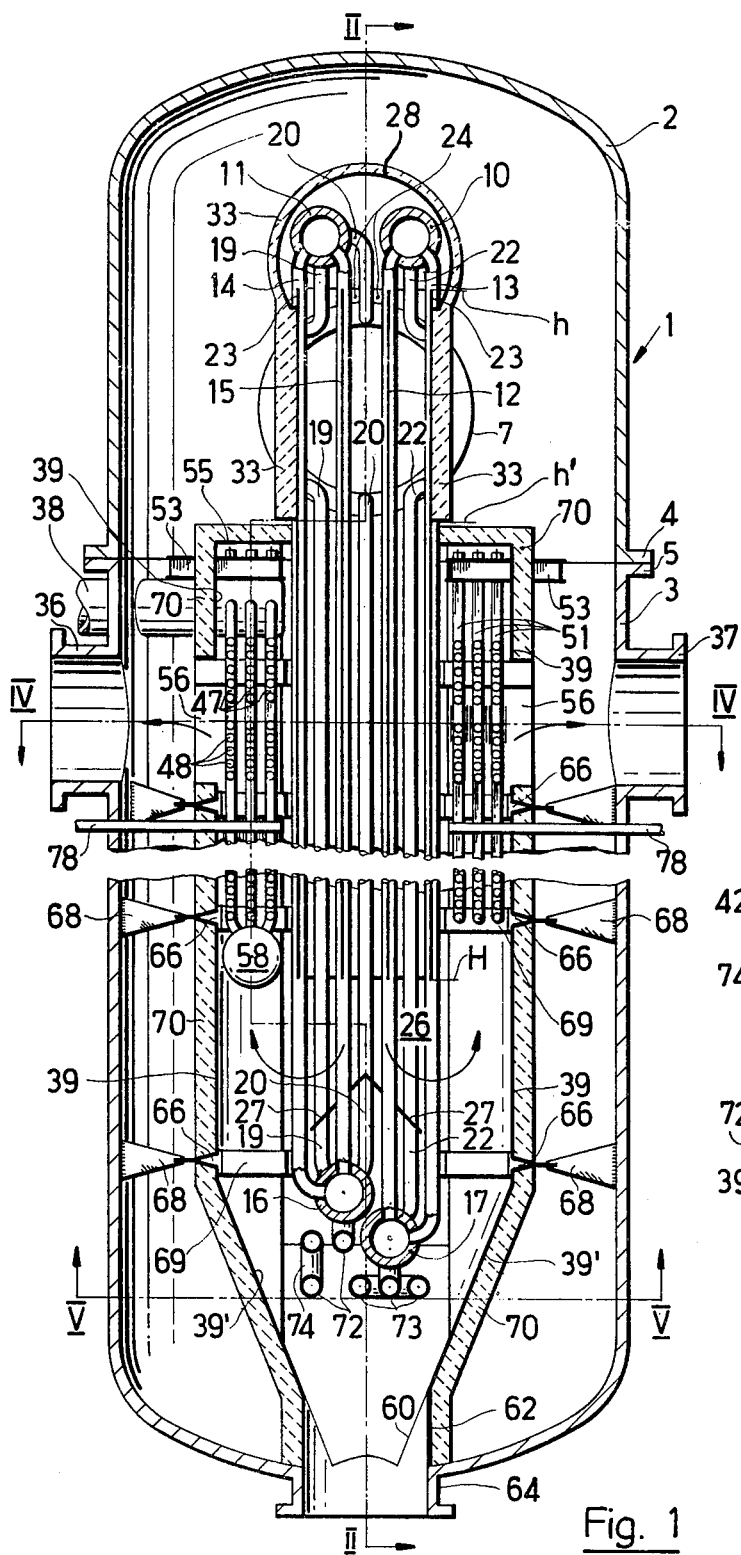
FIG. 1 illustrates a vertical cross-sectional view of a heat exchanger constructed in accordance with the invention as taken on line I—I of FIG. 2.

Referring to FIG. 1, the heat exchanger includes a central region which is not illustrated but which is several times the length of the top part and bottom part which are illustrated.

Figure 2:
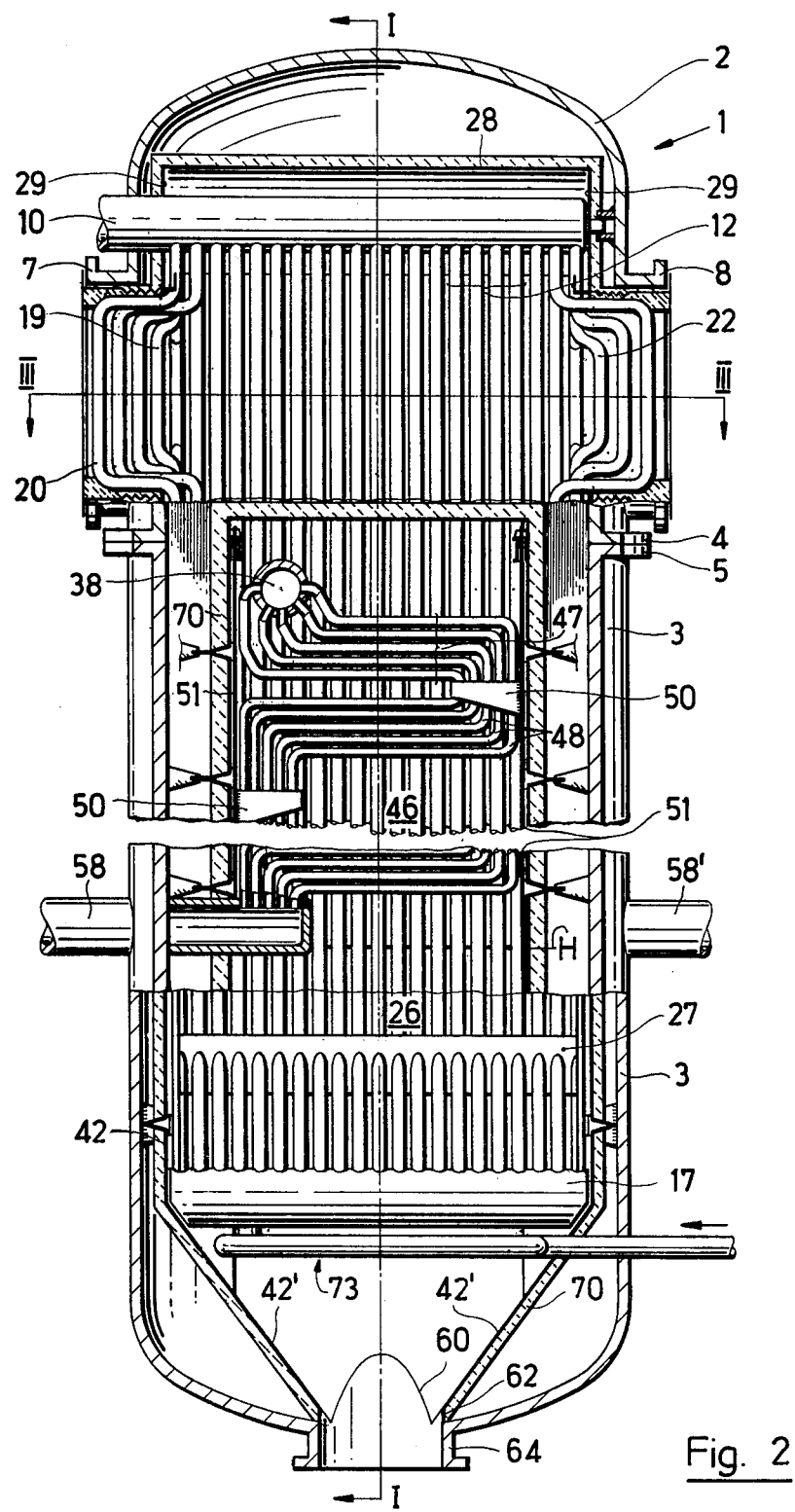
FIG. 2 is a vertical cross-sectional view taken on line II—II of FIG. 1.

Referring to FIG. 1, the heat exchanger includes a cylindrical pressure vessel 1 which comprises a top part 2 and a bottom part 3 which are releasably secured to each other in gas tight manner via flanges 4, 5. As indicated in FIG. 2, the top part 2 has a pair of entry spigots or beards 7, 8 which are disposed laterally opposite one another and through which hot gases containing solid particles may enter for cooling purposes. The bottom part 3 has two exit spigots or beards 36, 37 for the gases which are cooled within the heat exchanger. As indicated in FIG. 1, the exit spigots 36, 37 are disposed in a plane perpendicular to the common axis of the entry spigots 7, 8.

Referring to FIGS. 1 and 2, a pair of collectors 10, 11 extend through the top part 2 of the vessel parallel to the common axis of the spigots 7, 8 and from opposite directions. As indicated in FIG. 2, each collector 10, 11 extends substantially as far as the opposite wall of the top part 2. In addition, two tube rows 12, 13 are connected to the collector 10 while two tube rows 14, 15 are connected to the collector 11. Each of these rows 12-15 is comprised of a plurality of straight vertical tubes which extend downwardly into the bottom part 3 of the vessel. As indicated in FIG. 1, the bottom ends of the tubes of the rows 14, 15 extend to a top distributor 16 while the bottom ends of the tubes of the rows 12, 13 extend to a bottom distributor 17.

Figure 3:
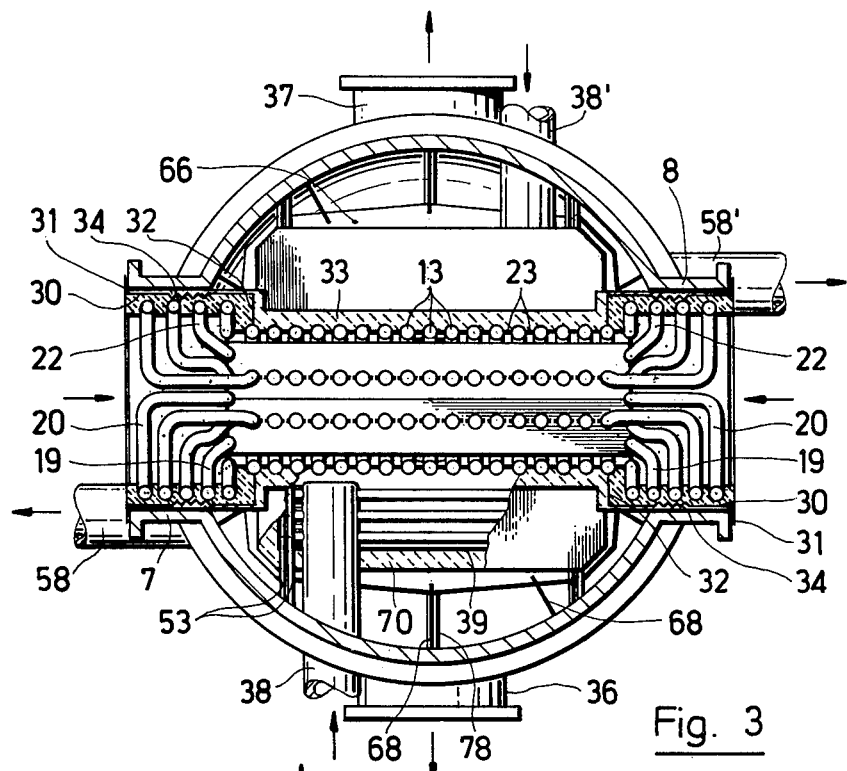
FIG. 3 illustrates a horizontal cross-sectional view taken on line III—III of FIG. 2.

Referring to FIGS. 1 and 3, a tube 19 is connected near both ends of the tube rows 14, 15 and between the outer most tubes thereof and extends downwardly to the distributor 16. Similarly, a tube 22 is connected near the two ends of the tube rows 12, 13 to the collector 10 and extends to the bottom distributor 17. A tube 20 is also disposed between the outer most tubes of the tube rows 12, 15 and near both ends thereof. Each tube 20 is connected at the top end to the collector 11 and at the bottom end to the top distributor 16.

The adjacent tubes of the outermost rows 13, 14 are sealingly connected by way of webs 23 in order to form two longitudinal walls of a faller column 25. These walls act as evaporator heating surfaces.

Figure 4:
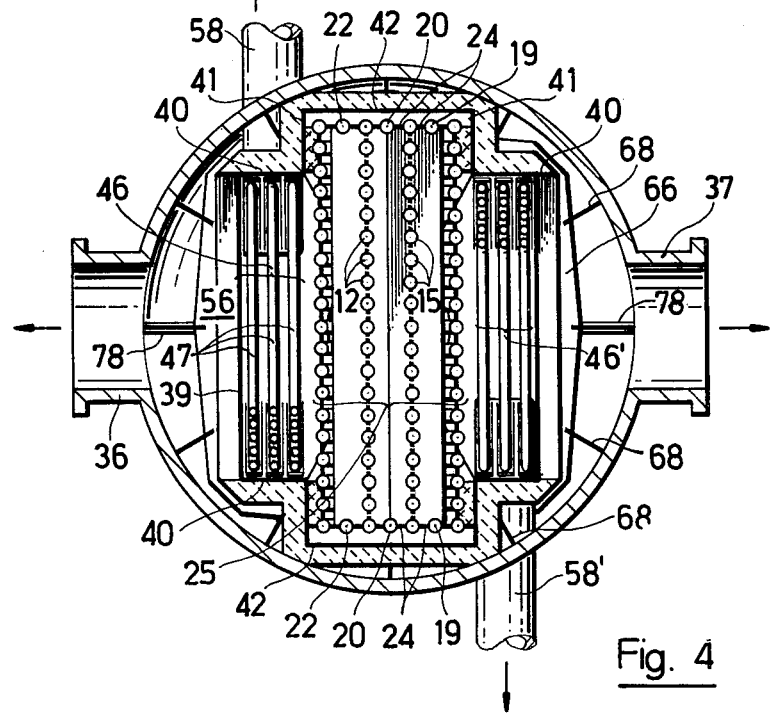
FIG. 4 illustrates a further horizontal cross-sectional view taken on line IV—IV of FIG. 1.

Referring to FIG. 4, the transverse walls of the faller column 25 are formed by the two outermost tubes of the rows 13, 12, 15, 14. To this end, these tubes are welded in seal tight fashion via webs 24 to the intermediate tubes 22, 20, 19. The resulting transverse walls define a rectangular cross-section with the outer walls of the faller column 25. The tube rows 12, 15 which extend within the faller column 25 form intermediate walls whose tubes have longitudinal fins which extend towards one another but which are not welded together.

Referring to FIGS. 1, 2 and 3, the two outermost tubes of the rows 12-15 and the two next-to-outermost tubes of the intermediate rows 12, 15 and the tubes 19, 20, 22 are so bent outwardly near the spigots 7, 8 as to follow the inner contour of the respective spigot 7, 8. These bent tube portions are slightly spaced from the spigots 7, 8 and substantially bound cylindrical cross-sections for the passage of the gases to be cooled. Consequently, for each entry spigot 7, 8, four tubes which start from the collector 10 are placed in one median spigot half (as shown in FIG. 2) while five tubes start from the collector 11 and are placed in the other median spigot half (see FIG. 3). As indicated, in FIG. 2, five tubes instead of four are shown near the entry spigot 7 in order to indicate the situation below the collector 11.

As indicated in FIGS. 1 and 2, the tubes which form the boundary walls of the faller column 25 are sealingly connected together only as far as the plane H. Below this plane, the tubes are webless and the tubes of the rows 12, 15 are without fins. Consequently, a deflecting chamber 26 is formed below the plane H from which gases may issue laterally in unhindered manner. In addition, a pair of inclined plates 27 are disposed a short distance above the distributors 16, 17 and below the plane H to prevent solid particles from being deposited on the distributors 16, 17 while also producing symmetrical flow conditions in the deflecting chamber 26.

Referring to FIG. 1, the webs 23, 24 between the tubes of the faller column terminate at the top in a plane h located within the top part 2 of the pressure vessel 1. In addition, a cylindrical metal hood 28 is sealingly connected to the longitudinal walls of the faller column 25 near the top end of the webs 23, 24. This metal hood 28 is welded at both end-face edges to a metal circular segment 29. The chord of each segment 29 is sealingly connected to the referred transverse wall of the faller column 25. As indicated, the hood and the longitudinal wall of the faller column 25 have external insulation 33 down to the lower level h'.

Referring to FIG. 3, a sleeve 30 is disposed in each entry spigot 7, 8 between the spigot 7,8 and the tubes which are bent to the inner contour of the spigots 7, 8. Each sleeve 30 has an outwardly directed flange 31 at the outer end while the inner end is connected in gas tight manner to the outermost tube of the tube row 13, 14 of the faller column 25. In addition, two circular metal portions 32 are inserted in each sleeve 30. In addition, each sleeve 30 has a bellows or boot part 34 to take-up differences in heat expansion. A curable insulating compound is also introduced between the tubes which are bent into the spigots 7, 8 and the sleeves 30. This insulating compound fills up the gaps between the tubes and thus provides considerable protection from the gas flowing through the spigots 7, 8.

Referring to FIGS. 1 and 3, two entry collectors 38, 38' extend through the pressure vessel 1 parallel to the exit spigots 36, 37 but laterally offset from the pressure vessel axis. These collectors 38, 38' are located above the exit spigots 36, 37 and below the flange 5 of the bottom part 3 while terminating shortly before the faller column longitudinal wall which is formed by the tube row 13, 14, respectively. The collectors 38, 38' also extend through a metal wall 39 within the pressure vessel 1 as indicated in FIG. 4, the two walls 39 together with four narrow metal walls 40, four narrow metal walls 41 and two metal walls 42 form a cruciform-section shaft or column. The faller column 25 extends through the central zone of this cruciform shaft.

A pair of riser columns 46, 46' are disposed laterally on opposite sides of the faller column 25 while remaining within the cruciform shaft formed by the walls 39-42.

Referring to FIGS. 1 and 2, each riser column 46, 46' includes a plurality of heating surfaces. As indicated, three heating surfaces or tube banks 47 are each in the form of five meandering tubes 48. These tubes 48 are connected at the top ends to the entry collector 38 or 38', respectively while the bottom ends are connected to two exit collectors 58, 58', respectively. The axes of the exit collectors 58, 58' extend parallel to the entry spigots 7, 8 but with a lateral offset from the pressure vessel axis. As indicated, the collectors 58, 58' extend through the bottom part 3 of the pressure vessel and through one metal wall 40 of the associated riser column 46, 46'.

Referring to FIG. 2, the meandering tubes 48 are supported at its vertical arms by carriers 50 which are suspended on twelve strips or bands 51. The bands 51 are, in turn, suspended on four pairs of brackets 53 which are welded to the top edge of the pressure vessel bottom part 3 and which extend through the walls 39

(see FIG. 1). Cover plates 55 are disposed above the place where the bands 51 are secured to the brackets 53 in order to close the riser columns 46, 46'. These cover plates 55 extend from the walls 39 to near the longitudinal walls of the faller column 25.

As indicated in FIG. 1, the walls 39 are formed with rectangular apertures 56 in registration with the exit spigots 36, 37. In addition, the walls 39, 42 merge into inclined walls 39', 42', respectively, near the distributors 16, 17 and are connected to a cylindrical member 62 within a penetration line 60. The cylindrical member 62 is, in turn, connected to a vertical spigot 64 of the pressure vessel 1.

The walls 39 to 42 are provided with a plurality of outwardly bent expansion corrugations or folds 66 which are of Y-shaped cross-section. As indicated in FIG. 1, each expansion corrugation 66 is secured in a substantially triangular support member 68 on the pressure vessel 1 and has a cover strip 69 bridged on the inside of the fold. This cover strip 69 is, for example, welded to all of the corrugations 66 and encompasses the inside of the walls 39 to 42.

The walls 39-42, cover plates 55, inclined walls 39', 42' and the cylindrical member 62 all have an outside layer 70 of insulation.

Figure 5:
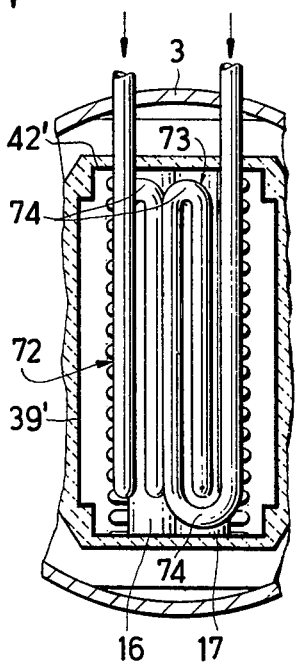
FIG. 5 illustrates a partial horizontal view taken on line V—V of FIG. 1.

Referring to FIGS. 1 and 5, an expansion loop (i.e. resilient line section) 72, 73 is connected to the underside of each distributor 16, 17 respectively. Each loop 72, 73 is comprised of three parallel arms and bends 74 which interconnect the arms. The last arm of the loops 72, 73 extends through one of the two walls 42' and through the pressure vessel 1 for connection to a feed line (not shown).

Because of the presence of the folds or corrugation 66, the walls 39 to 42 move little, if at all, lengthwise relative to the pressure vessel wall. Consequently soot blowers 78 can be provided which extend through the bottom part 3 of the pressure vessel and the walls 39 (only two of which are shown in FIGS. 1 and 4). These soot blowers 78 can be arranged to be either stationary or rotatable and/or movable lengthwise. Soot blowers of this kind or a shot-peening apparatus can be provided in the top part of the faller column 25 where expansion is hardly a problem.

The operation of the heat exchanger is as follows:

A hot gas which is to be cooled and which contains solid impurities enters the heat exchanger via the entry spigot 7, 8. The hot gases then descend through the faller column 25 and at the bottom most of the solid particles are discharged to the exterior via the inclined plates 27 and drop into the funnel shaped chamber defined by the inclined walls 39', 42'. The solids can be removed through the vertical spigot 64 of the pressure vessel 1 periodically or, if required, continuously. The gases which flow through the faller column 25 are then deflected upwardly in the deflecting chamber 26 with an additional separating effect occurring. The gases which now contain merely particles having a very low sink rate then rise through the riser columns 46, 46'. After being cooled by the heating surfaces within the riser columns 46, 46' the gases exit via the rectangular apertures 56 in the walls 39 and via the exit spigots 36, 37.

During operation, sensible heat of the gases entering the entry spigots 7, 8 is transferred to a working medium, such as water or water vapor. The water for evaporation enters the distributor 16, 17 via the expansion loops 72, 73 and then flows, preferrably by natural circulation, through the vertical tubes of the faller column 25. At this time, at least some evaporation occurs. The water then passes into the collectors 10, 11. Thereafter, the water leaves the pressure vessel 1 via the collectors 10, 11 and passes to a water separator or a drum of a drum boiler. The vapor which is then separated out passes into the entry collectors 38, 38' and is fed to the tubes 48 of the tube banks 47 for superheating. This superheated steam then passes into the collectors 58, 58' and exits from the pressure vessel 1, for example for supply to a load (not shown).

Of note, there would be virtually no deposition of solid particles in the space between the bottom part 3 of the pressure vessel and the inclined walls 39'. However, the small quantities of particles which may collect there can be readily removed manually since this gap is accessible via the exist spigots 36, 37.

In order to service the heat exchanger, the flanges 4, 5 are disconnected and the top part 2 and bottom part 3 are separated from one another. After one arm of the loop 72 and one arm of the loop 73 has been cut through, the top part 2 together with the two tube systems suspended on the collectors 10, 11 is drawn upwardly. Consequently, the space previously taken up by the faller column 25, becomes accessible. This also makes the riser columns 46, 46' and the tube banks 47 therein accessible for inspection and servicing work.

If it is necessary to inspect the faller column 25, the webs 24 between the two outermost tubes of the row 12 and the two tubes 20 are cut longitudinally so that the faller column 25 can be spread out like the shell of an oyster. Those tubes of the rows 12 and 15 which are not interconnected can be bent apart from one another so that the insides of the faller column longitudinal walls formed by the rows 13, 14 can be inspected.

Alternatively, the top part 2 of the pressure vessel can be suspended on a support structure so that the bottom part 3 can be moved downwardly for inspection purposes. In this case, the bottom part 3 can be formed by a number of separable sections in order to reduce the height of the support structure. Preferably, separate heating surfaces would be associated with the various sections so that the heat exchanger can be demounted without tube connections having to be broken between the sections inside the pressure vessel.

Alternatively, the exit spigots 36, 37 can be disposed in the bottom section of the bottom part 3. In combination with this arrangement, the cover plates 55 with their insulation 70 and the apertures 56 in the walls 39 can be omitted. Thus, the cooled gases may issue upwardly from the riser columns 46, 46' with a more uniform heating of the pressure vessel as a whole.

Further, instead of using a lateral supplied to the distributors, 16, 17, water or any other working medium can be supplied through one or more faller lines disposed in the pressure vessel 1 and extending through the top part 2.

The invention thus provides a heat exchanger of a construction which permits servicing of the various heat exchange surfaces of the riser columns and faller column to be performed in a relatively easy manner.

What is claimed is:

1. A heat exchanger for cooling a hot gas comprising
a pressure vessel having a top part and a bottom part releaseably secured to each other;
a faller column having a plurality of walls disposed in said top part and extending into said bottom part;

a plurality of heat exchange surfaces within said faller column walls and depending into said bottom part for cooling a flow of hot gas passing thereover;

at least one riser column having a plurality of walls secured to and disposed within said bottom part laterally of said faller column; and a plurality of heat exchange surfaces within said riser column walls for cooling a flow of gas passing thereover whereby upon separation and movement of said top part relative to said bottom part, said faller column can be withdrawn from said bottom part to permit access to said riser column.

2. A heat exchanger as set forth in claim 1 wherein said pressure vessel is cylindrical.

3. A heat exchanger as set forth in claim 1 which further comprises a deflecting chamber below said faller column and said riser column to receive solid particles deposited from the gas flow.

4. A heat exchanger as set forth in claim 1 further comprising a pair of said riser columns, said riser columns being disposed on opposite sides of said faller column in parallel relation.

5. A heat exchanger as set forth in claim 1 wherein said faller column walls are suspended on said top part of said pressure vessel.

6. A heat exchanger as set forth in claim 1 wherein said faller column walls include sealingly interconnected tubes forming an evaporator heating surface.

7. A heat exchanger as set forth in claim 6 which further comprises at least one distributor connected to said tubes at a lower end thereof, a feed line extending through said pressure vessel and a wall of said riser column to said distributor to deliver a working medium thereto, and a resilient line section connected between and to said feed line and said distributor.

8. A heat exchanger as set forth in claim 7 wherein said faller column includes a plurality of tubes forming intermediate walls and having lower ends connected to said distributor.

9. A heat exchanger as set forth in claim 6 wherein said faller column includes a plurality of tubes forming at least two intermediate walls and which further comprises a pair of distributors and a pair of collectors, some of said faller column walls and said intermediate walls being connected to and between one of said distributors and one of said collectors and the remainder of said faller column walls and said intermediate walls being connected to and between the other of said collectors and the other of said distributors.

10. A heat exchanger as set forth in claim 1 wherein said riser column walls are vertically resilient relative to said pressure vessel for taking up heat expansion and are connected to said pressure vessel to be vertically stationary.

11. In a heat exchanger for cooling a hot gas, the combination comprising a pressure vessel having a top part and a bottom part releaseably secured to each other;

a faller column having a plurality of walls disposed in said top part and extending into said bottom part for guiding a flow of hot gas downwardly; and at least one riser column having a plurality of walls secured to and disposed within said bottom part laterally of said faller column for guiding a flow of hot gas from said faller column upwardly whereby upon separation and movement of said top part relative to said bottom part, said faller column can be withdrawn from said bottom part to permit access to said riser column.

12. The combination as set forth in claim 11 wherein said faller column walls are suspended on said top part of said pressure vessel for movement therewith.

13. The combination as set forth in claim 11 further comprising a pair of said riser columns, said riser columns being disposed on opposite sides of said faller column in parallel relation.

* * * * *